(12) United States Patent
Klostranec et al.

(10) Patent No.: US 12,290,357 B2
(45) Date of Patent: May 6, 2025

(54) APPARATUS AND METHOD FOR CALCULATING A VOLUME FLOW RATE OF OXYGENATED BLOOD

(71) Applicant: FLOW CPR INC., Toronto (CA)

(72) Inventors: Jesse M. Klostranec, Toronto (CA); Emidio Tarulli, Kingston (CA)

(73) Assignee: FLOW CPR INC., Toronto (CA)

( * ) Notice: Subject to any disclaimer, the term of this patent is extended or adjusted under 35 U.S.C. 154(b) by 729 days.

(21) Appl. No.: 17/427,312

(22) PCT Filed: Jan. 31, 2020

(86) PCT No.: PCT/IB2020/050806
§ 371 (c)(1),
(2) Date: Jul. 30, 2021

(87) PCT Pub. No.: WO2020/157724
PCT Pub. Date: Aug. 6, 2020

(65) Prior Publication Data
US 2022/0125356 A1    Apr. 28, 2022

Related U.S. Application Data

(60) Provisional application No. 62/799,221, filed on Jan. 31, 2019.

(51) Int. Cl.
*A61B 5/1455* (2006.01)
*A61B 5/00* (2006.01)
*A61B 5/0265* (2006.01)

(52) U.S. Cl.
CPC ........ *A61B 5/14551* (2013.01); *A61B 5/0265* (2013.01); *A61B 5/6822* (2013.01);
(Continued)

(58) Field of Classification Search
CPC .............. A61B 5/1455; A61B 5/14551; A61B 5/14552; A61B 5/14532; A61B 5/0265;
(Continued)

(56) References Cited

U.S. PATENT DOCUMENTS 5,496,257 A   3/1996   Kelly
6,615,064 B1  9/2003   Aldrich
(Continued)

FOREIGN PATENT DOCUMENTS

CN   101309646 A   11/2008
CN   105636512 A    6/2016
(Continued)

OTHER PUBLICATIONS

ISA/CA, International Search Report and Written Opinion, Apr. 24, 2020 re PCT International Patent Application No. PCTIB2020050806.
(Continued)

*Primary Examiner* — Chu Chuan Liu
(74) *Attorney, Agent, or Firm* — Perry + Currier Inc.

(57) ABSTRACT

An apparatus and method for calculating a volume flow rate of oxygenated blood is provided. The apparatus includes a support configured to be removable adhered at a target region; an optical sensor secured to the support to detect an absorption of light by blood flowing through the target region for determining a blood oxygenation percentage; a magnetic sensor secured to the support to detect changes in a magnetic field in the target region for determining a flow rate; and a processor coupled to at least one of the optical sensor and the magnetic sensor for determining the blood oxygenation percentage, the flow rate, and a volume flow rate of oxygenated blood flowing through the target region based on the blood oxygenation percentage and the flow rate.

21 Claims, 6 Drawing Sheets

(52) U.S. Cl.
CPC .......... *A61B 5/6833* (2013.01); *A61B 5/7405* (2013.01); *A61B 5/742* (2013.01); *A61B 5/746* (2013.01); *A61B 2560/0214* (2013.01)

(58) Field of Classification Search
CPC ..... A61B 5/0261; A61B 5/0263; A61B 5/027; A61B 5/0275; A61B 5/6822; A61B 5/6833; A61B 5/762; A61B 5/746; A61B 5/7405

See application file for complete search history.

(56) References Cited

U.S. PATENT DOCUMENTS

| | | | |
|---|---|---|---|
| 7,190,999 | B2 | 3/2007 | Geheb et al. |
| 8,010,190 | B2 | 8/2011 | Olson et al. |
| 8,996,090 | B2 | 3/2015 | Anderson et al. |
| 2004/0034294 | A1 | 2/2004 | Kimball et al. |
| 2007/0273504 | A1 | 11/2007 | Tran |
| 2009/0306489 | A1* | 12/2009 | Boppart ............. A61B 5/14551 600/324 |
| 2011/0060201 | A1 | 3/2011 | Marks et al. |
| 2011/0202495 | A1* | 8/2011 | Gawlick ................ A61B 5/412 600/301 |
| 2013/0006077 | A1 | 1/2013 | Lu et al. |
| 2013/0184544 | A1 | 7/2013 | Su et al. |
| 2015/0289838 | A1 | 10/2015 | Nichol et al. |
| 2015/0351647 | A1 | 12/2015 | Dantu et al. |
| 2016/0169838 | A1* | 6/2016 | Nagarkar ............. A61B 5/0205 600/301 |
| 2016/0199251 | A1 | 7/2016 | Aelen et al. |
| 2017/0055904 | A1* | 3/2017 | Iizuka .................... A61B 5/318 |
| 2017/0281023 | A1 | 10/2017 | Freeman |

FOREIGN PATENT DOCUMENTS

| | | |
|---|---|---|
| CN | 106999067 A | 8/2017 |
| EP | 2545852 A1 | 1/2013 |
| JP | H05176916 A | 7/1993 |
| JP | 2001112725 A | 4/2001 |
| JP | 2005535407 A | 11/2005 |
| JP | 2017536904 A | 12/2017 |
| KR | 20180031991 A | 3/2018 |
| WO | WO-0033053 A1 | 6/2000 |
| WO | WO-2008084464 A1 | 7/2008 |
| WO | WO-2016094127 A1 | 6/2016 |

OTHER PUBLICATIONS

Phua, Chee Teck et al. "Non-invasive measurement of blood flow using magnetic disturbance method." 2009 International Conference on Biomedical and Pharmaceutical Engineering. IEEE, 2009. Abstract.

PCT/IB2020/050806, Apparatus and Method for Calculating a Volume Flow Rate of Oxygenated Blood.

Lee et al. "Magneto-plethysmographic sensor for peripheral blood flow velocity." IEEE Sensors journal 14.5 (2014): 1341-1342.

Ren, Yongjian, Practical Encyclopedia of Measurement Management, Section 8 , Flow Measurement, Science and Technology Press, p. 951, Feb. 28, 1990 with English translation.

* cited by examiner

APPARATUS AND METHOD FOR CALCULATING A VOLUME FLOW RATE OF OXYGENATED BLOOD

FIELD

The specification relates generally to medical devices, and more particularly to an apparatus and method for calculating a volume flow rate of oxygenated blood in a target region of tissue of a human.

BACKGROUND

Cardiopulmonary resuscitation (CPR) of patients is a common event in medical practice, with a reported occurrence rate of 400,000 per year in the United States alone. Guidelines, such as those provided by the American Heart Association, typically provide an algorithm for a rescuer to provide chest compressions and ventilation to perform CPR. Such algorithms may have different efficacy for different patients having different patient physiologies.

SUMMARY

An aspect of the specification is directed to an apparatus for calculating a volume flow rate of oxygenated blood. The apparatus includes a support having a first side and a second side opposite the first side, the support configured to be removably adhered to a skin of a human adjacent a target region of tissue. The apparatus further includes an optical sensor secured to the support at the second side of the support to detect an absorption of light by blood flowing through the target region for determining a blood oxygenation percentage of the blood flowing through the target region. The apparatus further includes a magnetic sensor secured to the support at the second side of the support to detect changes in a magnetic field in the target region for determining a flow rate of the blood flowing through the target region. The apparatus further includes a processor secured to the support and coupled to at least one of the optical sensor and the magnetic sensor for determining the blood oxygenation percentage and the flow rate and calculating a volume flow rate of oxygenated blood flowing through the target region based on the blood oxygenation percentage and the flow rate.

Another aspect of the specification is directed to a method for calculating a volume flow rate of oxygenated blood. The method includes detecting, at an optical sensor secured to a second side of a support of an apparatus, an absorption of light by blood flowing through a target region of tissue of a human, the absorption of light for determining a blood oxygenation percentage of the blood flowing through the target region. The method further includes detecting, at a magnetic sensor secured to the second side of the support, changes in a magnetic field in the target region for determining a flow rate of the blood flowing through the target region. The method further includes at a processor secured to the support, calculating, based on the blood oxygenation percentage and the flow rate, a volume flow rate of oxygenated blood flowing through the target region.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, ZZ, and the like). Similar logic can be applied for two or more items in any occurrence of "at least one . . . " and "one or more . . . " language.

The terms "about", "substantially", "essentially", "approximately", and the like, are defined as being "close to", for example as understood by persons of skill in the art. In some implementations, the terms are understood to be "within 10%," in other implementations, "within 5%", in yet further implementations, "within 1%", and in yet further implementations "within 0.5%".

BRIEF DESCRIPTION OF DRAWINGS

Implementations are described with reference to the following figures, in which.

DETAILED DESCRIPTION

Studies have shown improved outcomes when "patient-focused" physiologic measures are used to guide resuscitation efforts. In particular, real-time monitoring of diastolic blood pressure and/or capnographic $ET_{CO2}$ to direct CPR has demonstrated improved patient survival and discharge rates. Approximately 50% of cardiac arrests are treated by first responder emergency medical service personnel outside of a controlled hospital setting. In such acute circumstances, insertion of invasive physiologic monitors during concurrent CPR is challenging and impractical, leading to suboptimal outcomes. Accordingly, there is a need for non-invasive technologies to provide rescuers real-time measurements of clinically relevant patient physiology.

Figure 1:
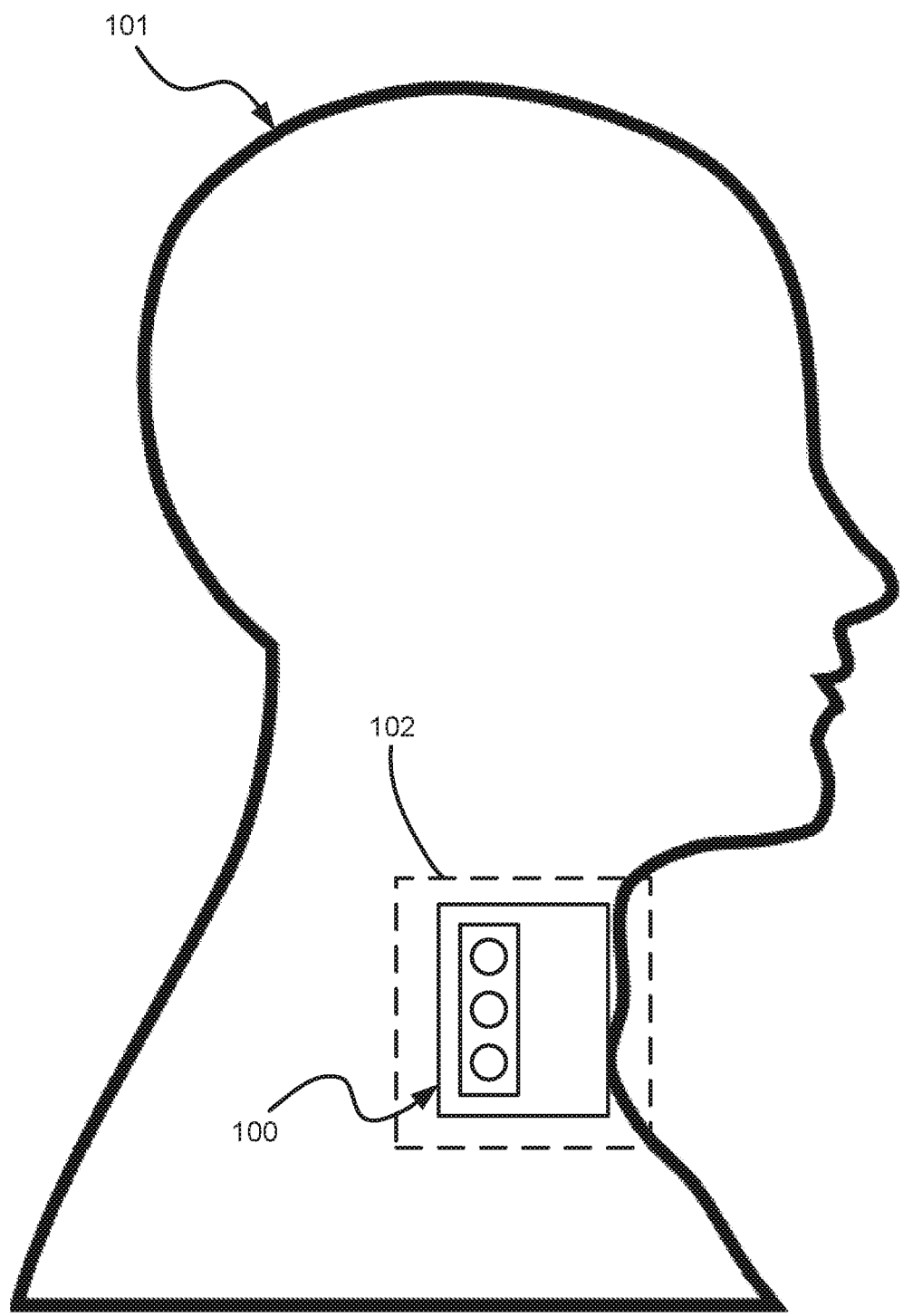
FIG. 1 depicts a schematic of an example apparatus adhered to a human for calculating a volume flow rate of oxygenated blood in use.

FIG. 1 depicts a schematic of an apparatus 100 for calculating a volume flow rate of oxygenated blood according to the present disclosure. The apparatus 100 is removably adhered to a skin of a human 101 adjacent a target region of tissue 102. In the present implementation, the target region 102 is at least partially in a neck of the human 101. In particular, the target region 102 includes a volume of tissue in the neck within range of sensors of the apparatus 100. For example, the target region 102 may include a portion of tissue in the neck including a portion of the carotid artery and/or the jugular vein. The target region 102 may include tissue directly abutting the apparatus 100 (i.e. including the region of skin to which the apparatus 100 is adhered), or the target region 102 may include tissue adjacent, but spaced away from the apparatus 100 (i.e. tissue within the human 101, but not including the region of skin to which the apparatus 100 is adhered, or other peripheral regions of tissue). In some implementations, two or more apparatuses 100 may be adhered in a bilateral configuration across the neck of the human 101, for example, to allow the two or more target regions 102 to measure a volume flow rate of oxygenated blood across two carotid arteries (i.e. containing approximately 80% of blood flow to the brain).

Figure 2:
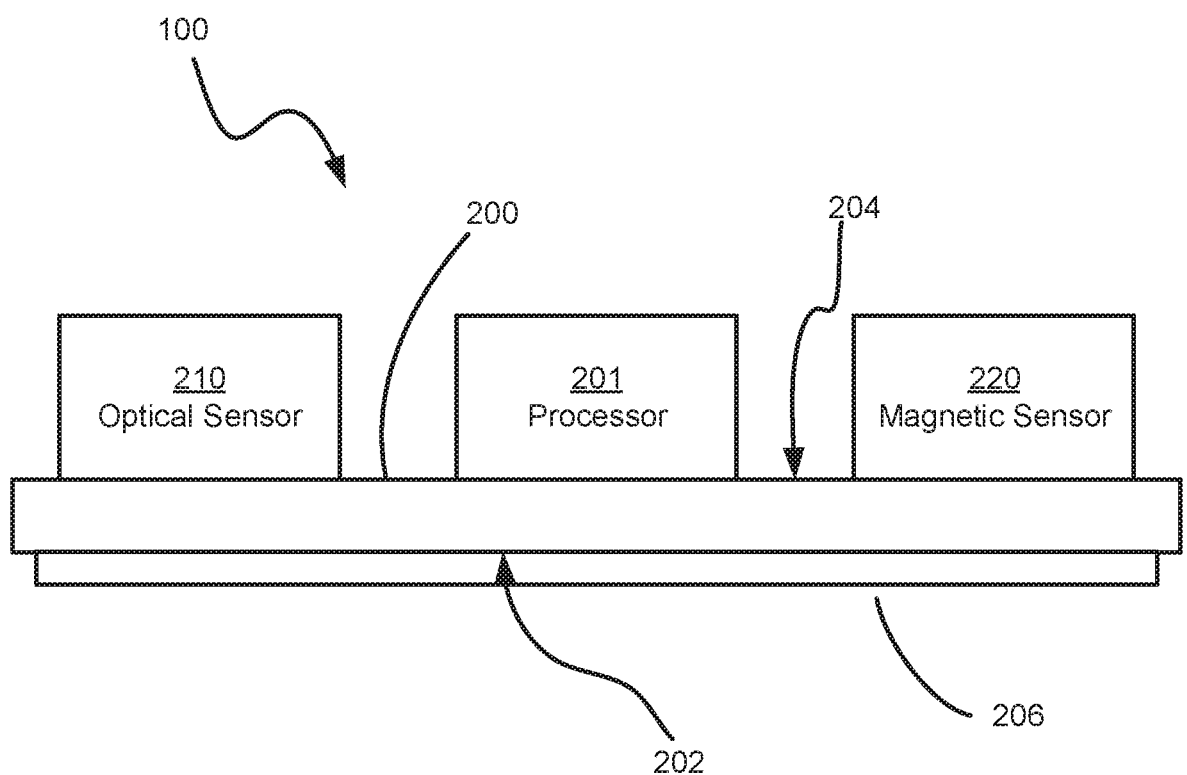
FIG. 2 depicts a schematic of the apparatus of FIG. 1.

Referring to FIG. 2, a schematic diagram of the apparatus 100 is shown. The apparatus 100 includes a support 200 configured to support the internal components of the apparatus 100. The support 200 has a first side 202 and a second side 204 opposite the first side. For example, the support 200 may include a pad or patch including one or more layers of material to support the internal components between the layers. The support 200 may include a flexible material such as a woven fabric, plastic (e.g. PVC, polyethylene or polyurethane), latex, or other materials suitable for contact with human skin, and flexible to conform to contours at the target region 102. The apparatus 100 also includes an adhesive layer 206 secured to the first side 202 of the support 200 to removably adhere the apparatus 100 to the skin of the human 101 at the target region 102. For example, the adhesive layer 206 may comprise acrylates (e.g. methacrylates, epoxy diacrylates, vinyl resins), or other suitable adhesive materials for removably adhering to human skin.

The apparatus 100 includes an optical sensor 210 secured to the support 200 at the second side 204. The optical sensor 210 is generally configured to detect an absorption of light by blood flowing through the target region 102 for determining a blood oxygenation percentage of the blood flowing through the target region 102, as will be described in greater detail herein. The apparatus 100 further includes a magnetic sensor 220 secured to the support 200 at the second side 204. The magnetic sensor 220 is generally configured to detect changes in a magnetic field in the target region 102 for determining a flow rate of blood flowing through the target region 102, as will be described in greater detail herein.

The apparatus 100 further includes a processor 201 secured to the support 200 at the second side 204. The processor 201 is coupled to at least one of the optical sensor 210 and the magnetic sensor 220. The processor 201 may include a central-processing unit (CPU), a microcontroller, a microprocessor, a processing core, a field-programmable gate array (FPGA), or similar. The processor 201 is generally configured to control the components of the apparatus 100, including the optical sensor 210 and the magnetic sensor 220 to perform the functionality described herein. The processor 201 is further configured to determine the blood oxygenation percentage and the flow rate, and to calculate the volume flow rate of oxygenated blood flowing through the target region 102 based on the blood oxygenation percentage and the flow rate.

Figure 3:
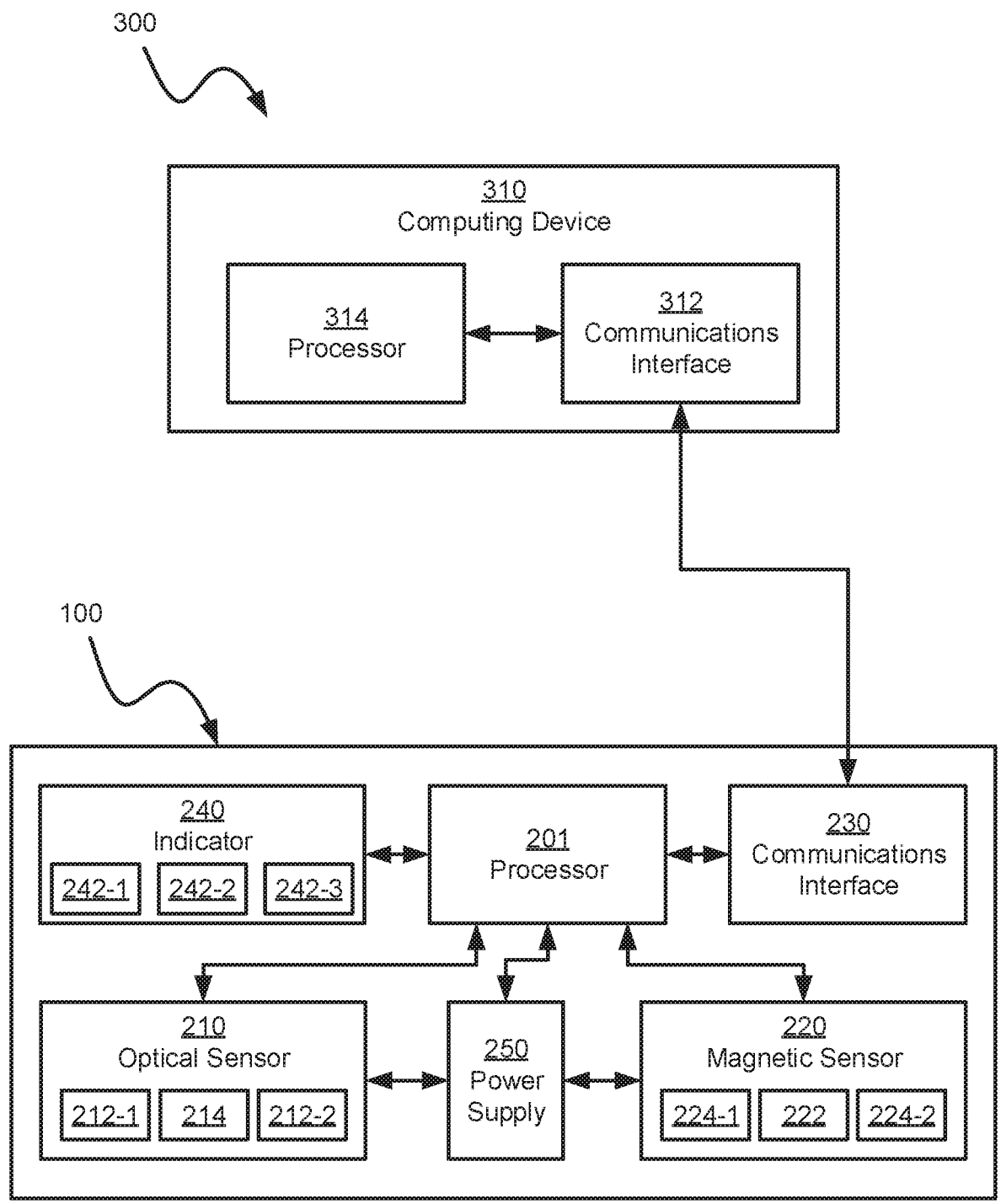
FIG. 3 depicts a block diagram of the apparatus of FIG. 1 according to another example implementation.

FIG. 3 depicts a block diagram of a system 300 including the apparatus 100 in communication with a computing device 310. The computing device 310 includes a communications interface 312 configured to communicate with the apparatus 100 and other computing devices. The computing device 310 further includes a processor 314 interconnected with the communications interface 312. The processor 314 may be configured to determine the blood oxygenation percentage, the flow rate, and the volume flow rate of oxygenated blood. The computing device 310 may be, for example, a desktop computer, a laptop computer, a tablet, a mobile phone, or other suitable device. The computing device 310 may further include a display (not shown) for displaying the volume flow rate of oxygenated blood, or another suitable indicator for generating notifications based on threshold conditions associated with the volume flow rate of oxygenated blood. For example, the computing device 310 can be a portable AED device, a component of a medical monitoring system, or the like.

In particular, the optical sensor 210 includes first and second light sources 212-1 and 212-2 (referred to generically as a light source 212, and collectively as light sources 212; this nomenclature is used elsewhere herein) configured to emit light at two different wavelengths in a direction away from the second side 204. The light sources 212 may be for example, light emitting diodes (LEDs), lasers, or the like. The optical sensor 210 further includes a receiver 214, such as a photodiode, configured to measure an absorption of light by the blood flowing through the target region 102. The first light source 212-1 is configured to emit light at the first wavelength $\lambda_1$ (e.g. about 905 nm (within the infrared range)) and the second light source 212-2 is configured to emit light at a second wavelength $\lambda_2$ (e.g. about 660 nm (within the red range)). In operation, the processor 201 is configured to control the optical sensor 210, and in particular the light sources 212 to simultaneously emit light at the two different wavelengths $\lambda_1$ and $\lambda_2$. The receiver 214 therefore measures reflected light of the first wavelength $\lambda_1$ and reflected light of the second wavelength $\lambda_2$, from which a first absorption of light of the first wavelength $\lambda_1$ and a second absorption of light of the second wavelength $\lambda_2$ may be calculated.

More generally, the apparatus 100 includes a suitable device configured to measure oxygen saturation or percentage. For example, the apparatus 100 can include a peripheral pulse oximeter instead of or in addition to the optical sensor 210. In other examples, end tidal CO2 measurements (ET-CO2), for example as measured in intubated patients, may also be used to instead of or in addition to the optical sensor 210 to measure oxygen saturation or percentage.

The magnetic sensor 220 includes a magnet 222 configured to induce a magnetic field in the target region 102 and at least two magnetic detectors 224-1 and 224-2 configured to detect changes in the magnetic field at the target region 102. The magnet 222 may be a permanent magnet such as a bar magnet or may be an electromagnet. For example, the processor 201 may control a power supply 250 to produce a current to induce a magnetic field at the magnet 222. In some implementations, the magnetic sensor 220 includes two or more magnets 222. For example, the magnetic sensor 220 can include two or more magnets 222 spatially arranged relative to the magnetic detectors 224 to achieve a more homogeneous magnetic field. Specifically, two magnets 222 may be arranged on opposite sides of the magnetic detectors 224.

In some implementations, the magnetic sensor 220 can include three or more magnetic detectors 224 to allow the apparatus 100 to determine a depth of the vessel through which blood is flowing using triangulation, as will be described further below. In other implementations, the magnetic sensor 220 includes only two magnetic detectors 224, for example if the vessel is superficial (e.g. the radial artery).

In still further implementations, the magnetic sensor 220 may include a magnet supported on a deformable material, such as a foam, gel, or the like, Upon detection of a magnetic force, the magnet may cause the deformable material to mechanically deflect, thus allowing the detected magnetic force to be determined. Specifically, the mechanical deflection of the deformable material may be proportional to the magnetic force.

In the present implementation, the apparatus 100 further includes a communications interface 230 coupled to the processor 201. The communications interface 230 is generally configured to allow the apparatus 100 to communicate with other computing devices such as the computing device 310. For example, the apparatus 100 may be configured to communicate, via the communications interface 230, the absorption of light and the changes in the magnetic field to an external processor for determining the blood oxygenation percentage and the flow rate, and for calculating a volume flow rate of oxygenated blood flowing through the target region based on the blood oxygenation percentage and the flow rate. The communications interface 230 may include a wireless transmitter (e.g. a Bluetooth® transmitter) or other suitable hardware for allowing the apparatus 100 to communicate with other computing devices.

In the present implementation, the apparatus 100 further includes an indicator 240 and the power supply 250. The indicator 240 is generally configured to generate a notification based on the volume flow rate of oxygenated blood. The indicator 240 is interconnected with the processor 201, which is configured to control the indicator 240 to generate the notifications. The notifications may include one or more of: an auditory signal and a visual signal. For example, the indicator 240 includes LED lights 242-1, 242-2, and 242-3. Each LED light 242 may correspond to a different notification and may be configured to emit different wavelengths of light (i.e. different colours). In particular, the processor 201 may be configured to control the indicator 240 to emit different signals via the LED lights 242 upon detection of various different threshold conditions associated with the volume flow rate of oxygenated blood, as will be described further below. In other implementations, the indicator 240 may include a speaker, and the signal may be an auditory signal. For example, the auditory signal may include three different tones, messages or instructions based on the different threshold conditions.

The power supply 250 is electrically connected to the optical sensor 210 and the magnetic sensor 220 and is generally configured to supply power to the optical sensor 210 and the magnetic sensor 220. The power supply 250 is also interconnected with the processor 201, which is configured to control the power supply 250.

Figure 4:
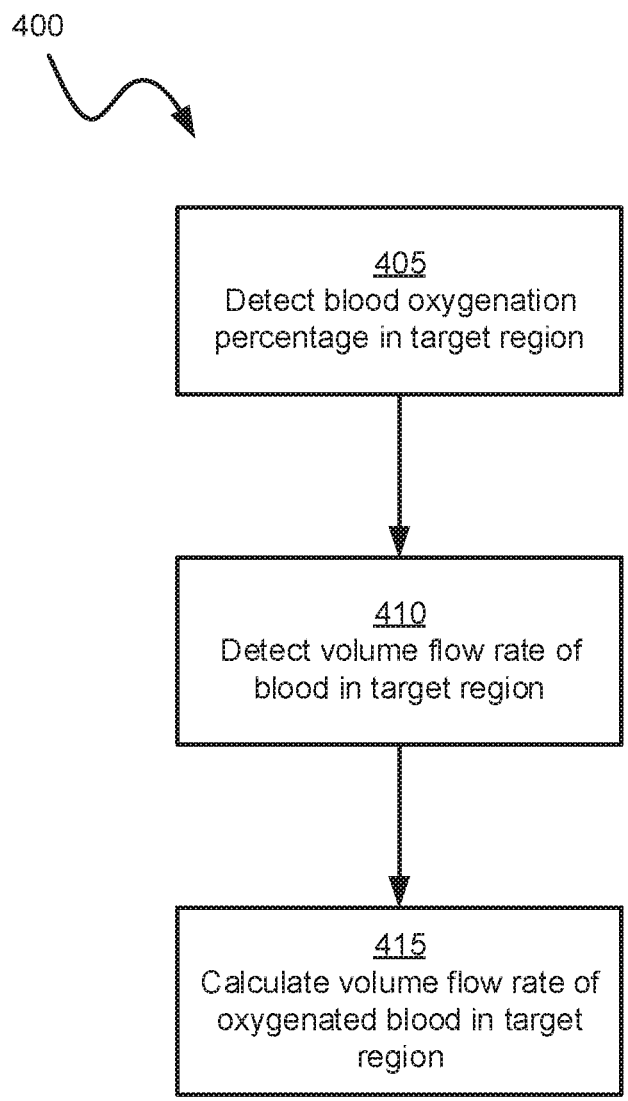
FIG. 4 depicts a flowchart of an example method of calculating a volume flow rate of oxygenated blood.

Turning now to FIG. 4, an example method 400 for calculating the volume flow rate of oxygenated blood in the target region is depicted. For ease of description, the method 400 will be described in connection with the apparatus 100 as illustrated in FIG. 1 and FIG. 2. In some implementations, the method 400 may also be implemented or performed using another suitable system.

At block 405, the optical sensor 210 detects an absorption of light by blood flowing through the target region 102. In particular, the receiver 214 measures a first absorption of light of the first wavelength $\lambda_1$ and a second absorption of light of the second wavelength $\lambda_2$. In some implementations, the first and second absorption values are communicated to the processor 201 for further processing. In other implementations, the first and second absorption values are communicated to the computing device 310 via the communications interface 230 for further processing.

At block 410, the magnetic sensor 220 detects changes in the magnetic field in the target region 102. The changes in magnetic field may also be communicated to the processor 201 or the computing device 310 for further processing.

At block 415, the volume flow rate of oxygenated blood flowing through the target region 102 is calculated. In particular, the volume flow rate of oxygenated blood is calculated based on blood oxygenation percentage and flow rate. In the present implementation, block 415 will be described in connection with its performance by the processor 201. In other implementations, block 415 may be performed by the computing device 310, and in particular, the processor 314, or other suitable systems.

The processor 201 is configured to determine the blood oxygenation percentage of blood flowing through the target region 102 based on the absorption of light as detected by the optical sensor 210 at block 405. The blood oxygenation percentage may be determined based on a ratio of absorbance of light of a first wavelength $\lambda_1$ and a light of a second wavelength $\lambda_2$. In particular, the concentrations of oxyhemoglobin (i.e. oxygenated blood) and deoxyhemoglobin (i.e. deoxygenated blood) may be calculated based on the absorption of light of wavelengths $\lambda_1$ and $\lambda_2$ and predefined parameters for describing light absorption by oxyhemoglobin and deoxyhemoglobin. The blood oxygenation percentage may then be determined based on the ratio of the concentration of oxygenated blood to the sum of the concentrations of oxygenated and deoxygenated blood.

The processor 201 is further configured to determine the flow rate of blood flowing through the target region 102 based on changes in the magnetic field in the target region 102 as detected by the magnetic sensor 220 at block 410. The flow rate of blood flowing through the target region 102 may be determined based on the changes in magnetic field detected at the target region 102. Specifically, an integrated area under the curve per peak in the signal detected by the magnetic sensor 220 may be used, Oxyhemoglobin is diamagnetic, meaning that in the absence of an applied magnetic field, it exhibits zero net magnetic moment and only weakly creates an opposing magnetic moment to an applied external field. In contrast, deoxyhemoglobin is paramagnetic, meaning that application of an external magnetic field aligns the magnetic moment in-line with the field. Therefore, the presence of deoxyhemoglobin enhances the magnetic field (i.e. it increases magnetic flux density).

A net magnetization vector centered on the middle of the cross-section of a blood vessel may be defined based on a number of paramagnetic dipoles, and an effective volume of a dipole. The value of the net magnetization vector is a function of time since it varies with blood flow, with an amplitude of signal related to the change in magnetic flux density corresponds to the volume flow rate of blood through the vessel, given by multiplying the mean velocity of blood flow by the vessel cross-sectional area. When the velocity of blood flow is multiplied by the vessel cross-sectional area, it gives the volume flow rate of blood. The signal detected by the detectors 224 is proportional to the temporal variation in the net magnetization vector. In particular, the signal amplitude is dependent on the value of the net magnetization vector and the distance of the vessel from the detector 224. The geometric configuration of the detector 224 may therefore be used to localize the vessel.

Figure 5A:
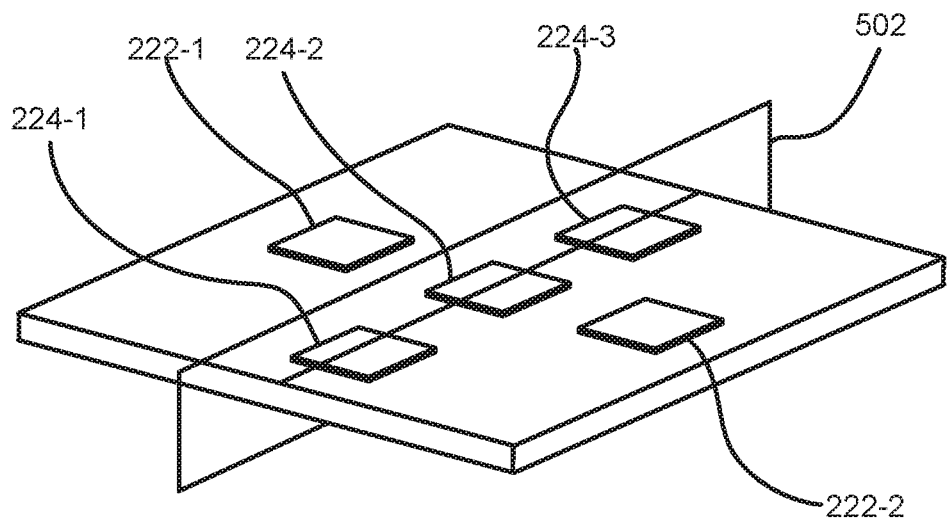
FIG. 5A depicts a perspective view of an example magnetic sensor of the apparatus of FIG. 1.
Figure 5B:
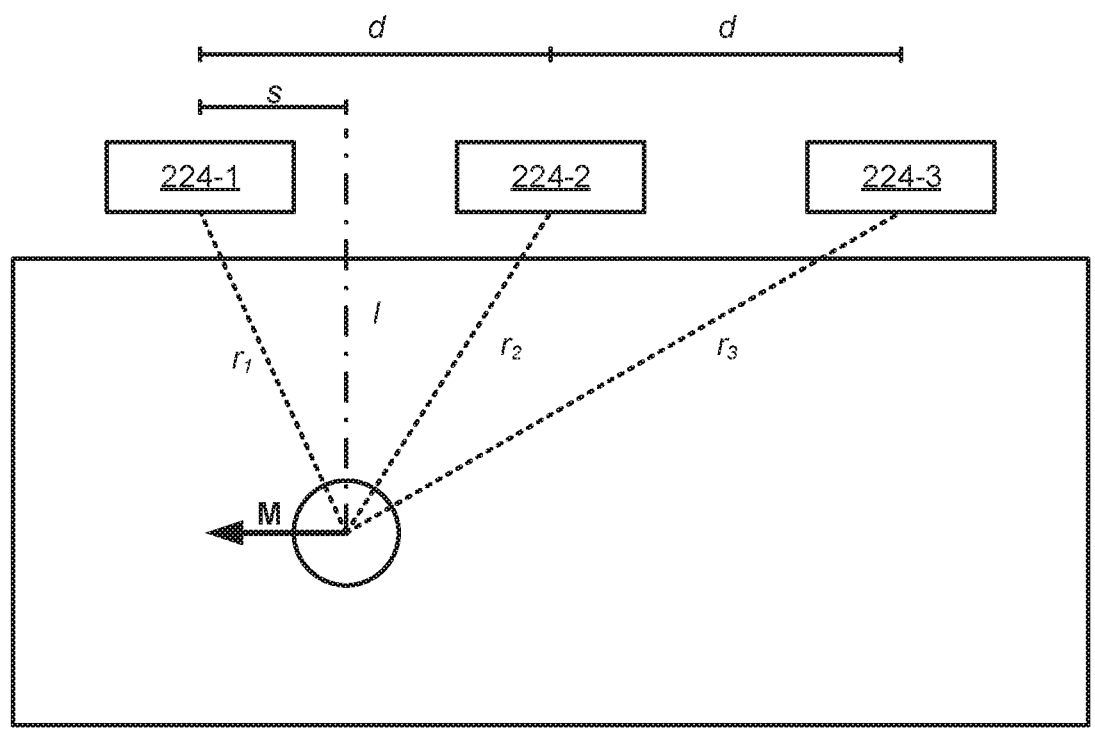
FIG. 5B depicts a cross-sectional view of the magnetic sensor of FIG. 5A.

For example, FIG. 5A depicts the magnetic detectors 224-1, 224-2 and a third magnetic detector 224-3 spaced in a plane 502 approximately perpendicular to the direction of the vessel, as well as magnets 222-1 and 222-2 to provide a homogenous magnetic field. This gives the geometric arrangement demonstrated in FIG. 5B. The value M represents the net magnetization vector. The values $r_1$, $r_2$ and $r_3$ represent the respective distances from the center of the vessel to each of the detectors 224. The value d represents the spacing between detectors 224, and the values s and l represent x and y coordinates of the center of the vessel relative to the first detector 224-1. The distances s and l may be determined based on amplitude of the changes detected by the magnetic detectors 224 and the geometric relationships between the detectors 224 and the vessel.

Having determined the placement of the vessel, the magnitude of the magnetic field generated by the magnet 222 may be determined based on the depth of the vessel. For example, a relationship between the depth of the vessel and the magnitude of the magnetic field may be prestored based on experimental data. Accordingly, the apparatus 100 may retrieve the magnitude of the magnetic field based on the determined depth of the vessel. Finally, the measured signal intensities may be correlated with the magnitude of the magnetic field to obtain a quantitative measure of the amount of paramagnetism present, which corresponds to the volume flow rate of deoxyhemoglobin.

In some implementations, the target region 102 may be the neck of a patient, and the apparatus 100 may be positioned over the carotid artery. Accordingly, the blood oxygenation percentage and the volume flow rate of deoxygenated blood may be used to calculate the overall volume flow rate and the volume flow rate of oxygenated blood. Conversely, the apparatus 100 may be positioned over the jugular veins to determine an overall volume flow rate (based on the jugular veins containing primarily deoxygenated blood) and calculate the volume flow rate of oxygenated blood based on the overall volume flow rate and the blood oxygenation percentage.

In some implementations, the processor 201 may further be configured to separate paramagnetic signals from the carotid artery and adjacent internal jugular veins using a Fourier analysis. In particular, high frequencies may be used to extract the carotid signal, while lower frequencies correspond to the flow through the jugular veins.

Figure 6:
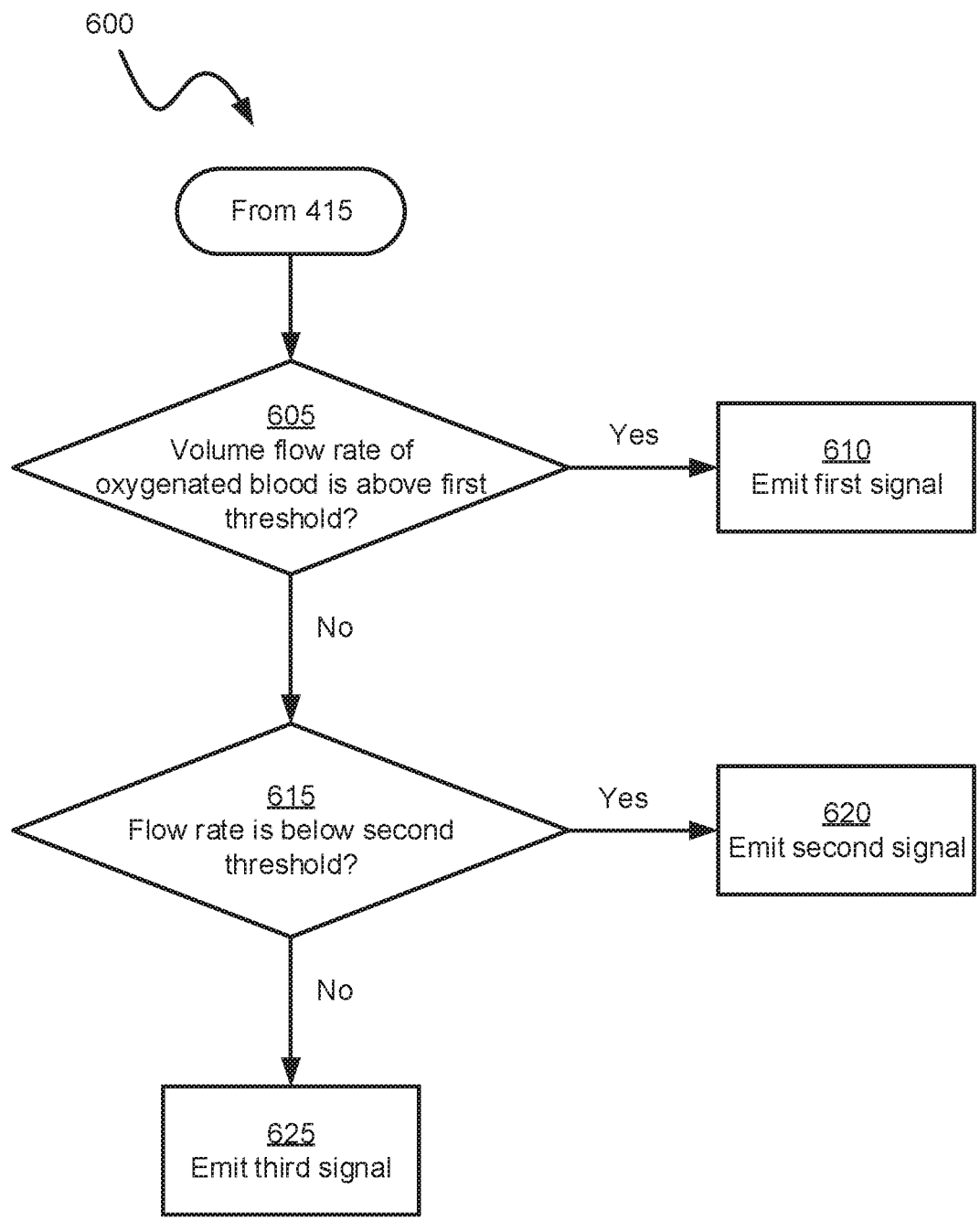
FIG. 6 depicts a flow chart of an example method for generating notifications based on the volume flow rate of oxygenated blood.

At block 415, the processor 201 may further be configured to control the indicator 240 to generate a notification based on the calculated volume flow rate of oxygenated blood. For example, the processor 201 may generate a notification according to the example method 600 depicted in FIG. 6.

At block 605, the processor 201 is configured to determine if the volume flow rate of oxygenated blood is above a first threshold. For example, the first threshold may represent a minimum desired volume of oxygenated blood. If the determination is affirmative, the processor 201 is configured to proceed to block 610. At block 610, the processor 201 is configured to control the LED light 242-1 to emit a first signal. For example, the first signal may be a green light, or an auditory signal indicating that the minimum desired volume of oxygenated blood is being achieved.

If the determination at block 605 is negative, the processor 201 is configured to proceed to block 615. At block 615, the processor 201 is configured to determine if the flow rate is below a second threshold. For example, the second threshold may represent a minimum desired flow rate. If the flow rate of blood in the target region is below the second threshold, the processor 201 is configured to proceed to block 620.

At block 620, the processor 201 is configured to control the LED light 242-2 to emit a second signal. For example, the second signal may be an orange light or an auditory signal indicating that the flow rate of blood in the target region should be increased (e.g. by increasing the rate or depth of compressions during CPR) in order to increase the volume flow rate of oxygenated blood.

If, at block 615, the processor 201 determines that the flow rate of blood in the target region is above the second threshold, the processor 201 is configured to proceed to block 625. At block 625, the processor 201 is configured to control the LED light 242-3 to emit a third signal. For example, the third signal may be a red light or an auditory signal indicating that the blood oxygenation percentage of blood in the target region should be increased (e.g. by providing ventilation to increase oxygen during CPR) in order to increase the volume flow rate of oxygenated blood.

The present disclosure provides an non-invasive apparatus and method for calculating the volume flow rate of oxygenated blood. The apparatus may be used, for example, during CPR to determine the amount of oxygen flowing through the neck. In particular, the volume flow rate of oxygenated blood flowing through the neck provides a good indication of the amount of oxygenated blood flowing to the brain. In particular, about 80% of cerebral blood flow is provided via the carotid arteries, hence measuring oxygenated blood in the carotid arteries provides a surrogate measure of cerebral perfusion achieved during CPR.

In some implementations, the apparatus itself may be compact and battery-powered, requiring no outside power sources and no additional devices for interpretation. In particular, the apparatus may include indicators, such as visual indicators configured to generate notifications based on the volume flow rate of oxygenated blood. For example, the apparatus may emit a first signal when the volume flow rate of oxygenated blood is sufficient for providing oxygen to the brain. The apparatus may emit a second signal when the volume flow rate of oxygenated blood and the flow rate are low, indicating that flow rate should be increased to increase the volume flow rate of oxygenated blood. For example, the apparatus may include an indicator to indicate to a rescuer that increased rate or depth of compressions is required. In other implementations, the second signal may be emitted when the volume flow rate of oxygenated blood is low and the blood oxygenation percentage is high, which similarly indicates that flow rate should be increased the volume flow rate of oxygenated blood. The apparatus may emit a third signal when the volume flow rate of oxygenated blood is low and the flow rate is high, indicating that blood oxygenation percentage should be increased. For example, the apparatus may include an indicator to indicate to a rescuer that ventilation is required to provide oxygen to the blood and hence increase the blood oxygenation percentage. In other implementations, the third signal may be emitted when the volume flow rate of oxygenated blood and the blood oxygenation percentage are low.

The apparatus therefore provides real-time monitoring of volume flow rate of oxygenated blood during CPR. Further, in some implementations, the calculation of the volume flow rate of oxygenated blood and the indicators are provided in the apparatus itself. The apparatus may therefore be used as a stand-alone assistive medical device to provide real-time feedback to the rescuer, with no wires or other connections required which may interfere or otherwise be disconnected during CPR.

Moreover, in some implementations, the apparatus includes a communications interface configured to wirelessly transmit data (e.g. via Bluetooth®, or another suitable wireless communication protocol) to an external computing device. In some implementations, the calculation of the volume flow rate of oxygenated blood may be provided in the apparatus itself. The apparatus may therefore be configured to communicate the results to the external computing device for display or further processing. In addition, in some implementations, the apparatus may be configured to communicate the detected absorption of light and changes in magnetic field to the external computing device for calculating the volume flow rate of oxygenated blood, display, and further processing. For example, the external computing device may display the values of the blood oxygenation percentage, flow rate and the volume flow rate of oxygenated blood. In addition to or instead of auditory or visual notifications, some implementations may provide real-time measurements of the volume flow rate of oxygenated blood to other devices, such as ventilation support machines, chest compression machines or other CPR assistive devices to allow for adjustments in their operation. That is, the operational parameters of CPR assistive device may be modified in real time in response to the volume flow rate of oxygenated blood to increase the efficacy of the assistive device in performing CPR.

In still further implementations, the apparatus may be used during other medical procedures, such as surgical procedures, to track volume flow rate of oxygenated blood to the brain or other major organs. For example, the apparatus may be used as a surrogate measure of cerebral blood flow (CBF) in neuro-intensive care unit patients with concern for increasing intracranial pressure (ICP). Specifically, as ICP increases, CBF decreases; accordingly, the apparatus may be used in a non-invasive manner by providing a real-time continuous monitoring for changes (decreases) in CBF in patients with clinical concern for developing increased ICP (e.g. head trauma patients). Thus invasive measures such as a burr hole with insertion of a probe into the brain parenchyma may be avoided. The apparatus may also assess ratios of volume flow rates of oxygenated blood to the brain from the right and left carotid arteries for use in detecting and monitoring acute ischemic stroke and carotid stenosis. In some implementations, the apparatus may also provide feedback suitable for use outside a hospital environment, for example, by patients as an at-home monitor of dialysis fistulas.

In other examples, the apparatus may be used to monitor issue oxygenation during peripheral revascularization procedures.

The scope of the claims should not be limited by the embodiments set forth in the above examples, but should be given the broadest interpretation consistent with the description as a whole.

The invention claimed is:

1. An apparatus comprising:
   a support having a first side and a second side opposite the first side, the support configured to be removably adhered to a skin of a human adjacent a target region of tissue;
   an optical sensor secured to the support at the second side of the support to detect an absorption of light by blood flowing through the target region for determining a blood oxygenation percentage of the blood flowing through the target region;
   a magnetic sensor secured to the support at the second side of the support to induce a magnetic field in the target region and to detect changes in the magnetic field at the target region corresponding to a presence of deoxyhemoglobin in blood, for determining a volume flow rate of deoxyhemoglobin flowing through the target region; and
   a processor secured to the support and coupled to the optical sensor and the magnetic sensor for determining the blood oxygenation percentage and the volume flow rate of deoxyhemoglobin and calculating a volume flow rate of oxygenated blood flowing through the target region based on the blood oxygenation percentage and the volume flow rate of deoxyhemoglobin.

2. The apparatus of claim 1, further comprising a power supply electrically connected to at least one of the optical sensor and the magnetic sensor, the power supply configured to supply power to the at least one of the optical sensor and the magnetic sensor.

3. The apparatus of claim 1, wherein the optical sensor comprises:
   a light source configured to emit light at two different wavelengths in a direction away from the second side; and
   a receiver configured to measure the absorption of light by the blood flowing through the target region.

4. The apparatus of claim 1, wherein the magnetic sensor comprises:
   a magnet configured to induce the magnetic field; and
   at least two magnetic detectors configured to detect the changes in the magnetic field at the target region.

5. The apparatus of claim 1 further comprising an indicator secured to the support at the second side and coupled to the processor, the indicator configured to generate a notification based on the volume flow rate of oxygenated blood.

6. The apparatus of claim 5, wherein the notification comprises one or more of: an auditory signal and a visual signal.

7. The apparatus of claim 5,
   wherein the processor is further configured to calculate an overall volume flow rate based on the volume flow rate of oxygenated blood and the blood oxygenation percentage; and
   wherein the indicator is configured to:
      emit a first signal when the volume flow rate of oxygenated blood is above a first threshold;
      emit a second signal when the volume flow rate of oxygenated blood is below the first threshold, and the overall volume flow rate is below a second threshold; and
      emit a third signal when the volume flow rate of oxygenated blood is below the first threshold, and the overall volume flow rate is above the second threshold.

8. The apparatus of claim 1, further comprising a communications interface secured to the support and coupled to at least one of the optical sensor, the magnetic sensor, and the processor, the communications interface configured to communicate at least one of the blood oxygenation percentage, the volume flow rate of deoxyhemoglobin, and the volume flow rate of oxygenated blood to an external processor.

9. The apparatus of claim 1, further comprising an adhesive layer secured to the first side of the support to removably adhere the support to the skin of the human adjacent the target region.

10. The apparatus of claim 1, wherein the target region is at least partially in a neck of the human.

11. A method comprising:
   detecting, at an optical sensor secured to a second side of a support of an apparatus, an absorption of light by blood flowing through a target region of tissue of a human, the absorption of light for determining a blood oxygenation percentage of the blood flowing through the target region;
   inducing, at a magnetic sensor secured to the second side of the support, a magnetic field in the target region;
   detecting, at the magnetic sensor, changes in the magnetic field in the target region corresponding to a presence of deoxyhemoglobin in blood for determining a volume flow rate of deoxyhemoglobin flowing through the target region; and at a processor secured to the support, calculating, based on the blood oxygenation percentage and the volume flow rate of deoxyhemoglobin, a volume flow rate of oxygenated blood flowing through the target region.

12. The method of claim 11, further comprising supplying power to at least one of the optical sensor and the magnetic sensor by a power supply electrically connected to the at least one of the optical sensor and the magnetic sensor.

13. The method of claim 11, wherein the detecting, at the optical sensor, the blood oxygenation percentage comprises:
emitting, by a light source, light at two different wavelengths in a direction away from the support; and
measuring, by a receiver, the absorption of light by the blood flowing through the target region.

14. The method of claim 11,
wherein the inducing, at the magnetic sensor, comprises inducing, by a magnet, the magnetic field in the target region; and
wherein the detecting, at the magnetic sensor, the volume flow rate of deoxyhemoglobin comprises detecting, by at least two magnetic detectors, the changes in the magnetic field at the target region.

15. The method of claim 11, further comprising generating a notification based on the volume flow rate of oxygenated blood.

16. The method of claim 15, wherein the notification comprises one or more of: an auditory signal and a visual signal.

17. The method of claim 15, further comprising calculating at the processor, an overall volume flow rate based on the volume flow rate of oxygenated blood and the blood oxygenation percentage;
wherein generating the notification comprises:
emitting a first signal when the volume flow rate of oxygenated blood is above a first threshold;
emitting a second signal when the volume flow rate of oxygenated blood is below the first threshold, and the overall volume flow rate is below a second threshold; and
emitting a third signal when the volume flow rate of oxygenated blood is below the first threshold, and the overall volume flow rate is above the second threshold.

18. The method of claim 11, further comprising communicating, via a wireless transmitter, the blood oxygenation percentage and the volume flow rate of deoxyhemoglobin to a second processor housed external to the apparatus to calculate the volume flow rate of oxygenated blood.

19. The method of claim 11, further comprising adhering the support to a skin of the human at the target region.

20. The method of claim 11, wherein the target region is a neck of the human.

21. An apparatus comprising:
a support having a first side and a second side opposite the first side, the support configured to be removably adhered to a skin of a human adjacent a target region of tissue
an optical sensor secured to the support at the second side of the support to detect an absorption of light by blood flowing through the target region for determining a blood oxygenation percentage of the blood flowing through the target region;
a magnetic sensor secured to the support at the second side of the support to induce a magnetic field in the target region and to detect changes in the magnetic field at the target region corresponding to a presence of deoxyhemoglobin in blood, for determining a volume flow rate of deoxyhemoglobin flowing through the target region; and
a communications interface coupled to the optical sensor and the magnetic sensor, the communications interface configured to communicate the absorption of light and the changes in the magnetic field to an external processor for determining the blood oxygenation percentage and the volume flow rate of deoxyhemoglobin and calculating a volume flow rate of oxygenated blood flowing through the target region based on the blood oxygenation percentage and the volume flow rate.

* * * * *